(12) United States Patent
Koseoglu

(10) Patent No.: US 11,230,676 B1
(45) Date of Patent: Jan. 25, 2022

(54) PROCESSES FOR PRODUCING PETROCHEMICAL PRODUCTS FROM CRUDE OIL

(71) Applicant: Saudi Arabian Oil Company, Dhahran (SA)

(72) Inventor: Omer Refa Koseoglu, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 0 days.

(21) Appl. No.: 17/146,979

(22) Filed: Jan. 12, 2021

(51) Int. Cl.
  *C10G 69/14* (2006.01)
  *C07C 4/06* (2006.01)
  *C07C 7/04* (2006.01)
  *C07C 7/00* (2006.01)

(52) U.S. Cl.
  CPC ........... *C10G 69/14* (2013.01); *C07C 4/06* (2013.01); *C07C 7/005* (2013.01); *C07C 7/04* (2013.01); *C10G 2300/107* (2013.01); *C10G 2300/202* (2013.01); *C10G 2300/205* (2013.01); *C10G 2300/206* (2013.01); *C10G 2300/301* (2013.01); *C10G 2300/308* (2013.01); *C10G 2300/4006* (2013.01); *C10G 2300/4012* (2013.01); *C10G 2300/4018* (2013.01); *C10G 2400/04* (2013.01)

(58) Field of Classification Search
  CPC ............. C10G 69/14; C10G 2300/301; C10G 2300/4018; C10G 2300/202; C10G 2400/04; C10G 2300/308; C10G 2300/107; C10G 2300/4006; C10G 2300/205; C10G 2300/206; C07C 7/04; C07C 7/005; C07C 4/06
  See application file for complete search history.

(56) References Cited

U.S. PATENT DOCUMENTS

| | | |
|---|---|---|
| 9,096,806 B2 | 8/2015 | Abba et al. |
| 9,228,139 B2 | 1/2016 | Shafi et al. |
| 9,228,140 B2 | 1/2016 | Abba et al. |
| 9,228,141 B2 | 1/2016 | Sayed et al. |
| 9,255,230 B2 | 2/2016 | Shafi et al. |
| 9,279,088 B2 | 3/2016 | Shafi et al. |
| 9,284,497 B2 | 3/2016 | Bourane et al. |
| 9,284,501 B2 | 3/2016 | Sayed et al. |

(Continued)

*Primary Examiner* — Thuan D Dang
(74) *Attorney, Agent, or Firm* — Dinsmore & Shol LLP

(57) ABSTRACT

According to one or more embodiments, presently disclosed are processes for producing petrochemical products from a hydrocarbon material. The process may include separating the crude oil into at least a lesser boiling point fraction and a greater boiling point fraction. At least 90 wt. % of the crude oil may be present in the combination of the greater boiling point fraction and the lesser boiling point fraction. The process may further include hydroprocessing the lesser boiling point fraction to form a first hydroprocessed effluent and hydroprocessing the greater boiling point fraction to form a second hydroprocessed effluent. The hydroprocessing of the lesser boiling point fraction may occur at a first pressure, the hydroprocessing of the lesser boiling point fraction may occur at a second pressure, and the second pressure may be at least 25 bar greater than the first pressure. The method may further include cracking at least a portion of the first hydroprocessed effluent and at least a portion of the second hydroprocessed effluent to form cracking reaction products.

20 Claims, 2 Drawing Sheets

(56) References Cited

U.S. PATENT DOCUMENTS

| | | |
|---|---|---|
| 9,284,502 B2 | 3/2016 | Bourane et al. |
| 9,290,705 B2 | 3/2016 | Bourane et al. |
| 9,296,961 B2 | 3/2016 | Shafi et al. |
| 9,382,486 B2 | 7/2016 | Bourane et al. |
| 9,587,185 B2 | 3/2017 | Shafi et al. |
| 9,771,530 B2 | 9/2017 | Sayed et al. |
| 10,011,788 B2 | 7/2018 | Sayed et al. |
| 10,017,704 B2 | 7/2018 | Shafi et al. |
| 10,221,365 B2 | 3/2019 | Bourane et al. |
| 10,233,400 B2 | 3/2019 | Bourane et al. |
| 10,246,651 B2 | 4/2019 | Bourane et al. |
| 10,329,499 B2 | 6/2019 | Shafi et al. |
| 10,344,227 B2 | 7/2019 | Shafi et al. |
| 10,494,574 B2 | 12/2019 | Akah et al. |
| 10,563,141 B2 | 2/2020 | Ding et al. |
| 10,689,585 B2 | 6/2020 | Shaik et al. |
| 10,689,587 B2 | 6/2020 | Al-Sayed et al. |
| 10,696,909 B2 | 6/2020 | Shaik et al. |
| 2018/0057758 A1 | 3/2018 | Al-Ghamdi et al. |
| 2018/0312767 A1* | 11/2018 | Al-Sayed .................. C01B 3/36 |
| 2018/0327677 A1 | 11/2018 | Ding et al. |

\* cited by examiner

PROCESSES FOR PRODUCING PETROCHEMICAL PRODUCTS FROM CRUDE OIL

TECHNICAL FIELD

Embodiments of the present disclosure generally relate to chemical processing and, more specifically, to processes and systems utilizing fluid catalytic cracking.

BACKGROUND

Ethylene, propylene, butylene, butadiene, and aromatics compounds such as benzene, toluene and xylenes are basic intermediates for a large proportion of the petrochemical industry. They are usually obtained through the thermal cracking (or steam pyrolysis) of petroleum gases and distillates such as naphtha, kerosene or even gas oil. These compounds are also produced through refinery fluidized catalytic cracking (FCC) process where classical heavy feedstocks such as gas oils or residues are converted. Typical FCC feedstocks range from hydrocracked bottoms to heavy feed fractions such as vacuum gas oil and atmospheric residue; however, these feedstocks are limited and/or may be more costly than other feedstock materials. The second most important source for propylene production is currently refinery propylene from FCC units. With the ever growing demand, FCC unit owners look increasingly to the petrochemicals market to boost their revenues by taking advantage of economic opportunities that arise in the propylene market.

The worldwide increasing demand for light olefins remains a major challenge for many integrated refineries. In particular, the production of some valuable light olefins such as ethylene, propylene, butylene has attracted increased attention as pure olefin streams are considered the building blocks for polymer synthesis. The production of light olefins depends on several process variables like the feed type, operating conditions, and the type of catalyst.

SUMMARY

Disclosed herein are embodiments of processes and systems for producing petrochemical products from crude oils. The embodiments include separating the crude oil stream into two streams (as least) and hydroprocessing those two streams separately prior to cracking. It is recognized that advantages are attained by utilizing two hydroprocessing reactors because the two hydroprocessing reactors in combination may have less capital cost than a single hydroprocessing reactor that could treat all of the crude oil. This aspect is due, in one or more embodiments, to one of the hydroprocessing reactors operating at reduced pressure.

According to one or more embodiments, petrochemical products may be formed from a hydrocarbon material by a process that may comprise separating the crude oil into at least a lesser boiling point fraction and a greater boiling point fraction. At least 90 wt. % of the crude oil may be present in the combination of the greater boiling point fraction and the lesser boiling point fraction. The process may further comprise hydroprocessing the lesser boiling point fraction to form a first hydroprocessed effluent and hydroprocessing the greater boiling point fraction to form a second hydroprocessed effluent The hydroprocessing of the lesser boiling point fraction may occur at a first pressure, the hydroprocessing of the lesser boiling point fraction may occur at a second pressure, and the second pressure may be at least 25 bar greater than the first pressure. The method may further comprise cracking at least a portion of the first hydroprocessed effluent and at least a portion of the second hydroprocessed effluent to form cracking reaction products.

According to one or more additional embodiments, petrochemical products may be formed from a hydrocarbon material by a process that may comprise separating the crude oil into at least a lesser boiling point fraction and a greater boiling point fraction. At least 90 wt. % of the crude oil may be present in the combination of the greater boiling point fraction and the lesser boiling point fraction. The process may further comprise hydroprocessing the lesser boiling point fraction to form a first hydroprocessed effluent and hydroprocessing the greater boiling point fraction to form a second hydroprocessed effluent. The hydroprocessing of the lesser boiling point fraction may occur at a first pressure, the hydroprocessing of the lesser boiling point fraction may occur at a second pressure, and the second pressure may be at least 25 bar greater than the first pressure. The process may further comprise passing at least a portion of the first hydroprocessed effluent to a first FCC unit and cracking at least a portion of the first hydroprocessed effluent in the first FCC unit and passing at least a portion of the second hydroprocessed effluent to a first FCC unit and cracking at least a portion of the second hydroprocessed effluent in the second FCC unit.

According to one or more yet additional embodiments, petrochemical products may be formed from a hydrocarbon material by a process that may comprise separating the crude oil into at least a lesser boiling point fraction and a greater boiling point fraction. At least 90 wt. % of the crude oil may be present in the combination of the greater boiling point fraction and the lesser boiling point fraction. The process may further comprise hydroprocessing the lesser boiling point fraction to form a first hydroprocessed effluent and hydroprocessing the greater boiling point fraction to form a second hydroprocessed effluent. The hydroprocessing of the lesser boiling point fraction may occur at a first pressure, the hydroprocessing of the lesser boiling point fraction may occur at a second pressure, and the second pressure may be at least 25 bar greater than the first pressure. The process may further comprise passing at least a portion of the first hydroprocessed effluent and at least a portion of the second hydroprocessed effluent to a separation unit to form a light fraction, a middle fraction, and a heavy fraction. The process may further comprise passing the light fraction to a first FCC unit and cracking the second hydroprocessed effluent in the first FCC unit and passing the heavy fraction to a second FCC unit and cracking the second hydroprocessed effluent in the second FCC unit.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
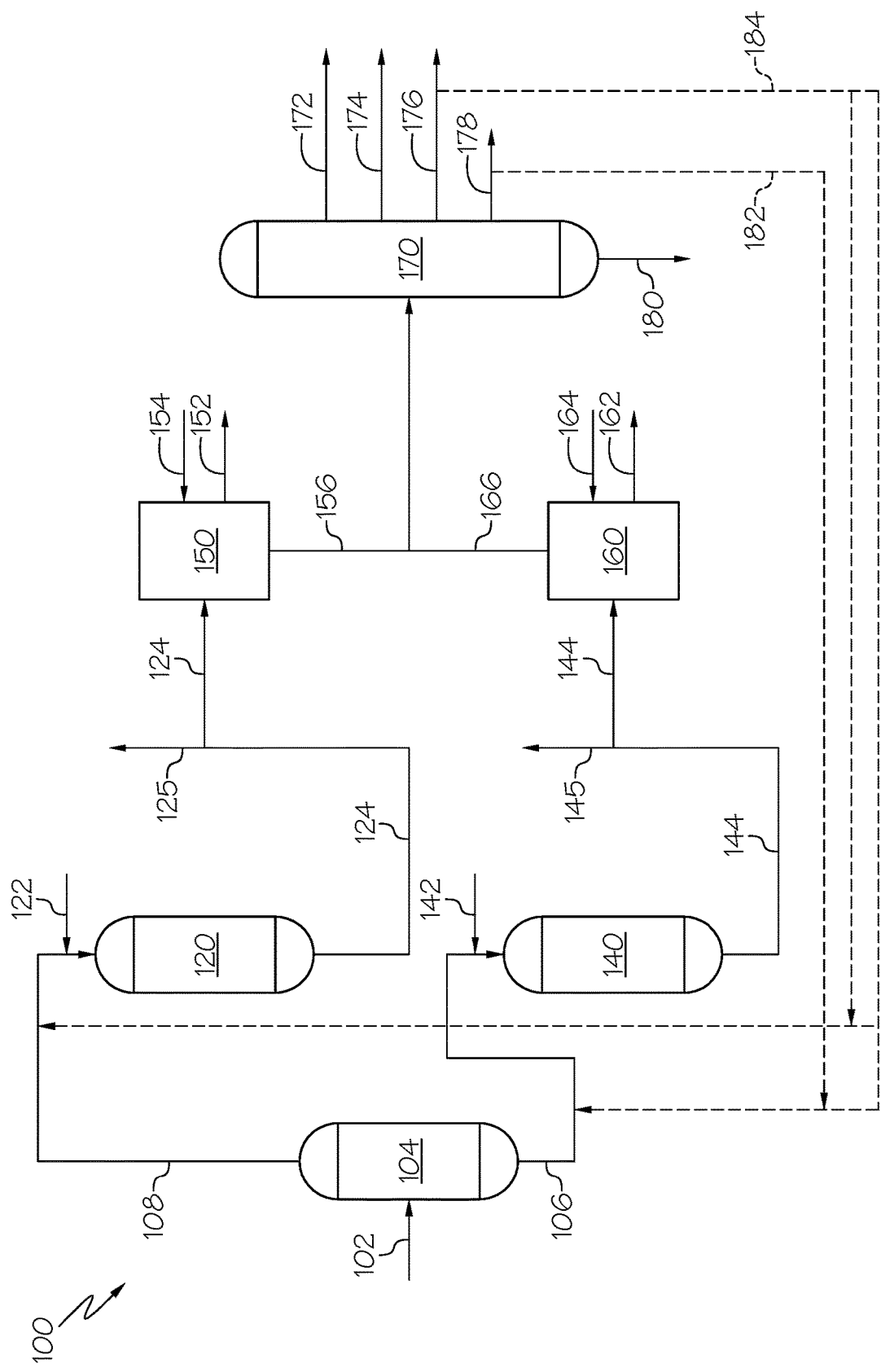
FIG. 1 is a generalized schematic diagram of a hydrocarbon feed conversion system, according to one or more embodiments described in this disclosure.

For the purpose of describing the simplified schematic illustrations and descriptions of the relevant figures, the numerous valves, temperature sensors, electronic controllers and the like that may be employed and well known to those of ordinary skill in the art of certain chemical processing operations are not included. Further, accompanying components that are often included in typical chemical processing operations, such as air supplies, catalyst hoppers, and flue gas handling systems, are not depicted. Accompanying components that are in hydrocracking units, such as bleed streams, spent catalyst discharge subsystems, and catalyst replacement sub-systems are also not shown. It should be understood that these components are within the spirit and scope of the present embodiments disclosed. However, operational components, such as those described in the present disclosure, may be added to the embodiments described in this disclosure.

It should further be noted that arrows in the drawings refer to process streams. However, the arrows may equivalently refer to transfer lines which may serve to transfer process streams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows which do not connect two or more system components signify a product stream which exits the depicted system or a system inlet stream which enters the depicted system. Product streams may be further processed in accompanying chemical processing systems or may be commercialized as end products. System inlet streams may be streams transferred from accompanying chemical processing systems or may be non-processed feedstock streams. Some arrows may represent recycle streams, which are effluent streams of system components that are recycled back into the system. However, it should be understood that any represented recycle stream, in some embodiments, may be replaced by a system inlet stream of the same material, and that a portion of a recycle stream may exit the system as a system product.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

Arrows shown in dashed line may signify optional streams or steps. However, it should be understood that not all solid lined arrows necessarily signify necessary streams or steps that would be present in all embodiments.

It should be understood that according to the embodiments presented in the relevant figures, an arrow between two system components may signify that the stream is not processed between the two system components. In other embodiments, the stream signified by the arrow may have substantially the same composition throughout its transport between the two system components. Additionally, it should be understood that in one or more embodiments, an arrow may represent that at least 75 wt. %, at least 90 wt. %, at least 95 wt. %, at least 99 wt. %, at least 99.9 wt. %, or even 100 wt. % of the stream is transported between the system components. As such, in some embodiments, less than all of the stream signified by an arrow may be transported between the system components, such as if a slip stream is present. For example, an arrow may signify that at least 75 wt. %, at least 90 wt. %, at least 95 wt. %, at least 99 wt. %, at least 99.9 wt. %, or even 100 wt. % of the stream is transported It should be understood that two or more process streams are "mixed" or "combined" when two or more lines intersect in the schematic flow diagrams of the relevant figures. Mixing or combining may also include mixing by directly introducing both streams into a like reactor, separation device, or other system component. For example, it should be understood that when two streams are depicted as being combined directly prior to entering a separation unit or reactor, that in some embodiments the streams could equivalently be introduced into the separation unit or reactor and be mixed in the reactor.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments of the present disclosure are directed to systems and processes for converting crude oil into chemical products. As is described herein, a crude oil stream may be separated into two streams, which are separately hydroprocessed to remove unwanted components of the crude oil. Following hydroprocessing, the hydroprocessed effluents are cracked, such as by fluidized catalytic cracking.

As used in this disclosure, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Example reactors include packed bed reactors such as fixed bed reactors, and fluidized bed reactors such as ebullated-bed or slurry phase reactors. One or more "reaction zones" may be disposed in a reactor. As used in this disclosure, a "reaction zone" refers to an area where a particular reaction takes place in a reactor. For example, a packed bed reactor with multiple catalyst beds may have multiple reaction zones, where each reaction zone is defined by the area of each catalyst bed.

As used in this disclosure, a "separation unit" refers to any separation device or system of separation devices that at least partially separates one or more chemicals that are mixed in a process stream from one another. For example, a separation unit may selectively separate differing chemical species, phases, or sized material from one another, forming one or more chemical fractions. Examples of separation units include, without limitation, distillation columns, flash drums, knock-out drums, knock-out pots, centrifuges, cyclones, filtration devices, traps, scrubbers, expansion devices, membranes, solvent extraction devices, and the like. It should be understood that separation processes described in this disclosure may not completely separate all of one chemical constituent from all of another chemical constituent. It should be understood that the separation processes described in this disclosure "at least partially" separate different chemical components from one another, and that even if not explicitly stated, it should be understood that separation may include only partial separation. As used in this disclosure, one or more chemical constituents may be "separated" from a process stream to form a new process stream. Generally, a process stream may enter a separation unit and be divided, or separated, into two or more process streams of desired composition. Further, in some separation processes, a "lesser boiling point fraction" (sometimes referred to as a "light fraction") and a "greater boiling point fraction" (sometimes referred to as a "heavy fraction") may exit the separation unit, where, on average, the contents of the lesser boiling point fraction stream have a lesser boiling point than the greater boiling point fraction stream. Other streams may fall between the lesser boiling point fraction and the greater boiling point fraction, such as an "intermediate boiling point fraction."

It should be understood that an "effluent" generally refers to a stream that exits a system component such as a separation unit, a reactor, or reaction zone, following a particular reaction or separation, and generally has a different composition (at least proportionally) than the stream that entered the separation unit, reactor, or reaction zone.

As used in this disclosure, a "catalyst" refers to any substance that increases the rate of a specific chemical reaction. Catalysts described in this disclosure may be utilized to promote various reactions, such as, but not limited to, cracking (including aromatic cracking), demetalization, desulfurization, and denitrogenation. As used in this disclosure, "cracking" generally refers to a chemical reaction where carbon-carbon bonds are broken. For example, a molecule having carbon to carbon bonds is broken into more than one molecule by the breaking of one or more of the carbon to carbon bonds, or is converted from a compound which includes a cyclic moiety, such as a cycloalkane, cycloalkane, naphthalene, an aromatic or the like, to a compound which does not include a cyclic moiety or contains fewer cyclic moieties than prior to cracking.

As used in this disclosure, the term "spent catalyst" refers to catalyst that has been introduced to and passed through a cracking reaction zone to crack a hydrocarbon material, such as the greater boiling point fraction or the lesser boiling point fraction for example, but has not been regenerated in the regenerator following introduction to the cracking reaction zone. The "spent catalyst" may have coke deposited on the catalyst and may include partially coked catalyst as well as fully coked catalysts. The amount of coke deposited on the "spent catalyst" may be greater than the amount of coke remaining on the regenerated catalyst following regeneration.

As used in this disclosure, the term "regenerated catalyst" refers to catalyst that has been introduced to a cracking reaction zone and then regenerated in a regenerator to heat the catalyst to a greater temperature, oxidize and remove at least a portion of the coke from the catalyst to restore at least a portion of the catalytic activity of the catalyst, or both. The "regenerated catalyst" may have less coke, a greater temperature, or both compared to spent catalyst and may have greater catalytic activity compared to spent catalyst. The "regenerated catalyst" may have more coke and lesser catalytic activity compared to fresh catalyst that has not passed through a cracking reaction zone and regenerator.

It should further be understood that streams may be named for the components of the stream, and the component for which the stream is named may be the major component of the stream (such as comprising from 50 weight percent (wt. %), from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream are disclosed as passing from one system component to another when a stream comprising that component is disclosed as passing from that system component to another. For example, a disclosed "propylene stream" passing from a first system component to a second system component should be understood to equivalently disclose "propylene" passing from a first system component to a second system component, and the like.

Figure 2:
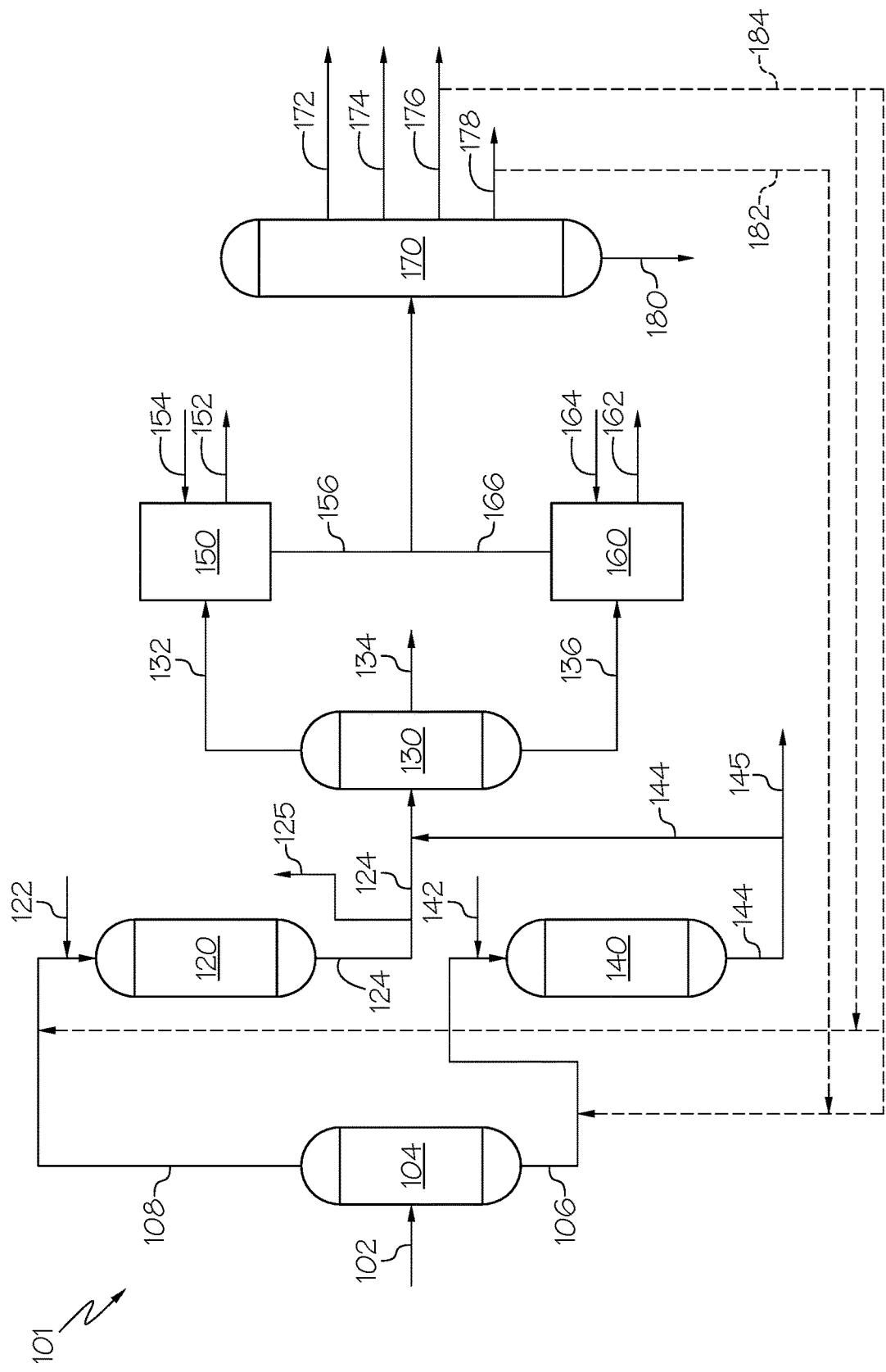
FIG. 2 depicts another generalized schematic diagram of a hydrocarbon feed conversion system according to one or more embodiments described in this disclosure.

Now referring to FIGS. 1 and 2, hydrocarbon feed conversion systems 100 and 200 are depicted. The hydrocarbon feed stream 102 may generally comprise a hydrocarbon material. In embodiments, the hydrocarbon material of the hydrocarbon feed stream may be crude oil. As used in this disclosure, the term "crude oil" is to be understood to mean a mixture of petroleum liquids, gases, solids, or combinations of these, including in some embodiments impurities such as sulfur-containing compounds, nitrogen-containing compounds and metal compounds that has not undergone significant separation or reaction processes. Crude oils are distinguished from fractions of crude oil. In certain embodiments the crude oil feedstock may be a minimally treated light crude oil to provide a crude oil feedstock having total metals (Ni+V) content of less than 5 parts per million by weight (ppmw) and Conradson carbon residue of less than 5 wt %.

The crude oil of the hydrocarbon feed stream 102 may have an American Petroleum Institute (API) gravity of from 10 degrees to 50 degrees, such as from 10 degrees to 20 degrees, from 20 degrees to 30 degrees, from 30 degrees to 40 degrees, from 40 degrees to 50 degrees, or any combination of these ranges. For example, the hydrocarbon feed stream 102 utilized may be an Arab heavy crude oil (API gravity of approximately 28°), Arab medium (API gravity of approximately 30°), Arab light (API gravity of approximately 33°), or Arab extra light (API gravity of approximately 39°). Example properties for one particular grade of Arab heavy crude oil are provided subsequently in Table 1.

TABLE 1

Example of Arab Heavy Crude Oil Feedstock

| Analysis | Units | Value |
| --- | --- | --- |
| American Petroleum Institute (API) gravity | degree | 27 |
| Density | grams per cubic centimeter (g/cm$^3$) | 0.8904 |
| Sulfur Content | weight percent (wt.%) | 2.83 |
| Nickel | parts per million by weight (ppmw) | 16.4 |
| Vanadium | ppmw | 56.4 |
| Sodium Chloride (NaCl) Content | ppmw | <5 |
| Conradson Carbon Residue | wt. % | 8.2 |
| C$_5$ Asphaltenes | wt. % | 7.8 |
| C$_7$ Asphaltenes | wt. % | 4.2 |

In general, the contents of the hydrocarbon feed stream 102 may include a relatively wide variety of chemical species based on boiling point. For example, the hydrocarbon feed stream 102 may have a composition such that the difference between the 5 wt. % boiling point and the 95 wt. % boiling point of the hydrocarbon feed stream 102 is at least 100° C., at least 200° C., at least 300° C., at least 400° C., at least 500° C., or even at least 600° C.

One or more supplemental feed streams (not shown) may be added to the hydrocarbon feed stream 102 prior to introducing the hydrocarbon feed stream 102 to the feed separator 104. As previously described, in one or more embodiments, the hydrocarbon feed stream 102 may be crude oil. In one or more embodiments, the hydrocarbon feed stream 102 may be crude oil, and one or more supplemental feed streams comprising one or more of a vacuum residue, tar sands, bitumen, atmospheric residue, vacuum gas oils, demetalized oils, naphtha streams, other hydrocarbon streams, or combinations of these materials, may be added to the crude oil upstream of the feed separator 104. Such a mixed feed stream 102 may be considered a crude oil since the added components may be present in crude oils.

The hydrocarbon feed stream 102 may be introduced to the feed separator 104 which may separate the contents of the hydrocarbon feed stream 102 into at least a greater boiling point fraction stream 106 and a lesser boiling point fraction stream 108. In one or more embodiments, at least 90 wt. %, at least 95 wt. %, at least 99 wt. %, or even at least 99.9 wt. % of the hydrocarbon feed stream may be present in the combination of the greater boiling point fraction stream 106 and a lesser boiling point fraction stream 108. The feed separator 104 is a separation unit. In one or more embodiments, the feed separator 104 may be a vapor-liquid separator such as a flash drum (sometimes referred to as a breakpot, knock-out drum, knock-out pot, compressor suction drum, or compressor inlet drum) with no theoretical plate. In other embodiments, the feed separator 104 may be a distillation unit with at least 1, at least 5, at least 10, or even at least 15 theoretical plates to have sharp separation between the fractions. In embodiments that utilize a vapor-liquid separator as the feed separator 104, the lesser boiling point fraction stream 108 may exit the feed separator 104 as a vapor and the greater boiling point fraction stream 106 may exit the feed separator 104 as a liquid. The vapor-liquid separator may be operated at a temperature and pressure suitable to separate the hydrocarbon feed stream 102 into the greater boiling point fraction stream 106 and the lesser boiling point fraction stream 108.

In one or more embodiments, the cut temperature or "cut point" (that is, the approximate atmospheric boiling point temperature separating the greater boiling point fraction stream 106 and the lesser boiling point fraction stream 108) of the vapor-liquid separator may be from 350° C. to 400° C. As such, all components of the lesser boiling point fraction stream 108 may have a boiling point (at atmospheric pressure) of less than or equal to 400° C., less than or equal to 390° C., less than or equal to 380° C., less than or equal to 370° C., or even less than or equal to 360° C., and all components of the greater boiling point fraction stream may have a boiling point (at atmospheric pressure) of at least 350° C., at least 360° C., at least 370° C., at least 380° C., or even at least 390° C.

In one or more embodiments, the cut point may be approximately 370° C. In such embodiments, naphtha and diesel fractions are present in the lesser boiling point fraction stream 108, and vacuum gas oils and vacuum residues may be present in the greater boiling point fraction stream 106.

Still referring to FIGS. 1 and 2, the lesser boiling point fraction stream 108 may be passed to a hydrotreater 120. The hydrotreater 120 may sometimes be referred to herein as a "mild hydrotreater" since utilizes relatively mild processing conditions as compared to hydrotreater 140. A hydrogen stream 122 may be mixed with the lesser boiling point fraction stream 108 to supply hydrogen to the hydrotreater 120. However, it is contemplated that in additional embodiments hydrogen may be supplied directly to the hydrotreater 120. The first hydroprocessed effluent 124 is passed out of the hydrotreater 120 following contact with catalyst in the hydrotreater 120.

In one or more embodiments, the primary purposes of the hydrotreater 120 may be to reduce sulfur and/or nitrogen content in the lesser boiling point fraction stream 108. In one or more embodiments, the hydrotreater 120 may reduce nitrogen content to less than or equal to 50%, less than or equal to 40%, less than or equal to 30%, less than or equal to 20%, or even less than or equal to 10% of the original content of nitrogen in the lesser boiling point fraction stream 108. For example, the hydrotreater 120 may reduce sulfur content to less than or equal to 50%, less than or equal to 40%, less than or equal to 30%, less than or equal to 20%, or even less than or equal to 10% of the original content of sulfur in the lesser boiling point fraction stream 108. That is, in some embodiments, the amount of nitrogen and/or sulfur in the first hydroprocessed effluent 124 may be less than that present in the lesser boiling point fraction stream 108 by the amounts described herein. For example, in one or more embodiments, the first hydroprocessed effluent 124 may have a concentration of nitrogen of less than or equal to 10 ppmw (parts per million by weight) and/or a concentration of sulfur of less than or equal to 10 ppmw.

The hydrotreater 120 may be a variety of reactor types, such as, without limitation, a fixed-bed, ebullated-bed, moving-bed, or slurry-bed. The hydrotreater 120 may comprise multiple beds in series. In some embodiments, a fixed-bed reactor may be desirable because it is more flexible than some other types of reactors because the feedstock can have a cycle length during the Turnaround & Inspection (T&I) cycles. In further embodiments, an ebullated-bed reactor may be desirable because it is more flexible than some other types of reactors because it can be run isothermally as the heat generated is quenched by the injection of cold feedstock.

The hydrotreater 120 may include one or more hydroprocessing catalysts that include one or more active metals and one or more supports. Without limitation, the active metals may be comprised of metals from IUPAC Groups 6, 8, 9, and 10, such as cobalt, nickel, molybdenum, or tungsten. The support materials may be chosen from, without limitation alumina, silica, titania, zeolites, or combination thereof. For example, in some embodiments, the catalyst of the hydrotreater 120 may comprise one metal from IUPAC Group 6 and one metal from IUPAC Groups 8-10. Example IUPAC Group 6 metals include molybdenum and tungsten. Example IUPAC Group 8-10 metals include nickel and cobalt.

For example, the catalyst of the hydrotreater 120 may comprise Ni and Mo on an alumina support (sometimes referred to as "Ni—Mo/$Al_2O_3$ catalyst"). The catalyst of the hydrotreater 120 may also contain a dopant that is selected from the group consisting of boron, phosphorus, halogens, silicon, and combinations thereof. In one or more embodiments, the catalyst of the hydrotreater 120 may comprise from 1 wt. % to 25 wt. % of an oxide or sulfide of molybdenum (such as from 11 wt. % to 17 wt. % or from 12 wt. % to 16 wt. % of an oxide or sulfide of molybdenum), from 1 wt. % to 7 wt. % of an oxide or sulfide of nickel (such as from 2 wt. % to 6 wt. % or from 3 wt. % to 5 wt. % of an oxide or sulfide of nickel), and from 75 wt. % to 89 wt. % of alumina (such as from 77 wt. % to 87 wt. % or from 79 wt. % to 85 wt. % of alumina). In some embodiments, the catalyst of the hydrotreater 120 may further comprise cobalt.

In one embodiment, the catalyst of the hydrotreater 120 may comprise nickel and molybdenum, and has a nickel to molybdenum mole ratio (Ni/(Ni+Mo)) of 0.1 to 0.3 (such as from 0.1 to 0.2 or from 0.2 to 0.3). In an embodiment that includes cobalt, the mole ratio of (Co+Ni)/Mo may be in the range of 0.25 to 0.85 (such as from 0.25 to 0.5 or from 0.5 to 0.85).

In another embodiment, the catalyst of the hydrotreater 120 may comprise Co and Mo on an alumina support. In one or more embodiments, the catalyst of the hydrotreater 120 may comprise from 1 wt. % to 25 wt. % of an oxide or sulfide of molybdenum (such as from 11 wt. % to 17 wt. % or from 12 wt. % to 16 wt. % of an oxide or sulfide of molybdenum), from 1 wt. % to 7 wt. % of an oxide or sulfide of cobalt (such as from 2 wt. % to 6 wt. % or from 3 wt. % to 5 wt. % of an oxide or sulfide of cobalt), and from 75 wt. % to 89 wt. % of alumina (such as from 77 wt. % to 87 wt. % or from 79 wt. % to 85 wt. % of alumina).

According to one or more embodiments, the hydrotreater 120 may have a weighted average bed temperature of from 300° C. to 450° C., such as from 320° C. to 380° C. The hydrotreater 120 may have a LHSV of 0.5/hour (inverse hours) to 10/hour, such as from 1/hour to 2/hour. The hydrotreater 120 may have a hydrogen to oil ratio of from 100 StLt per liters of oil to 5000 StLt per liters of oil, such as from 100 StLt per liters of oil to 1500 StLt per liters of oil.

Still referring to FIGS. 1 and 2, the greater boiling point fraction 108 may be passed to a hydrotreater 140. The hydrotreater 140 may sometimes be referred to herein as a "severe hydrotreater" since it utilizes relatively severe processing conditions as compared to hydrotreater 120. A hydrogen stream 142 may be mixed with the greater boiling point fraction stream 106 to supply hydrogen to the hydrotreater 140. However, it is contemplated that in additional embodiments hydrogen may be supplied directly to the hydrotreater 140. The hydroprocessed effluent 144 is passed out of the hydrotreater 140 following contact with catalyst in the hydrotreater 140.

In one or more embodiments, the primary purposes of the hydrotreater 140 may be to reduce metals, sulfur, nitrogen, and/or aromatics content in the greater boiling point fraction stream 108. In one or more embodiments, the hydrotreater 140 may reduce metals content to less than or equal to 50%, less than or equal to 40%, less than or equal to 30%, less than or equal to 20%, or even less than or equal to 10% of the original content of nitrogen in the greater boiling point fraction stream 108. In one or more embodiments, the hydrotreater 140 may reduce sulfur content to less than or equal to 50%, less than or equal to 40%, less than or equal to 30%, less than or equal to 20%, or even less than or equal to 10% of the original content of sulfur in the greater boiling point fraction stream 108. In one or more embodiments, the hydrotreater 140 may reduce nitrogen content to less than or equal to 50%, less than or equal to 40%, less than or equal to 30%, less than or equal to 20%, or even less than or equal to 10% of the original content of nitrogen in the greater boiling point fraction stream 108. In one or more embodiments, the hydrotreater 140 may reduce aromatics content to less than or equal to 50%, less than or equal to 40%, less than or equal to 30%, less than or equal to 20%, or even less than or equal to 10% of the original content of aromatics in the greater boiling point fraction stream 108. In one or more embodiments, the hydrotreater 140 may reduce asphaltene content to less than or equal to 50%, less than or equal to 40%, less than or equal to 30%, less than or equal to 20%, or even less than or equal to 10% of the original content of asphaltene in the greater boiling point fraction stream 108. That is, in some embodiments, the amount of nitrogen, metals, asphaltenes, aromatics, and/or sulfur in the second hydroprocessed effluent 144 may be less than that present in the greater boiling point fraction stream 108 by the amounts described herein. In one or more embodiments, the concentration of sulfur in the hydroprocessed effluent 144 may be less than or equal to 1000 ppmw, and/or the concentration of nitrogen in the hydroprocessed effluent 144 may be less than or equal to 1000 ppmw.

The hydrotreater 140 may be a variety of reactor types, such as, without limitation, a fixed-bed, ebullated-bed, moving-bed, or slurry-bed. The hydrotreater 140 may comprise multiple beds in series. In some embodiments, an ebullated-bed reactor may be desirable because it is more flexible than some other types of reactors because catalyst can be added and withdrawn from the ebullated-bed reactor, enabling the operator to have a cycle length during Turnaround & Inspection (T&I) cycles. In further embodiments, an ebullated-bed reactor may be desirable because it is more flexible than some other types of reactors because it can be run isothermally as the heat generated is quenched by the injection of cold feedstock. It should be appreciated that, in some embodiments, it may be desirable to have a fixed bed reactor as hydrotreater 120 and an ebullated bed reactor as hydrotreater 140.

The hydrotreater 140 may include one or more hydroprocessing catalysts that include one or more active metals and one or more supports. Without limitation, the active metals may be comprised of metals from IUPAC Groups 6, 8, 9, and 10, such as cobalt, nickel, molybdenum, or tungsten. The support materials may be chosen from, without limitation alumina, silica, titania, zeolites, or combination thereof. It is recognized that zeolite supports may be undesirable since asphaltenes present in the greater boiling point fraction stream 108 may poison such a catalyst, and some catalysts of the hydrotreater 140 may be sufficiently void of zeolite. For example, in some embodiments, the catalyst of the hydrotreater 140 may comprise one metal from IUPAC Group 6 and one metal from IUPAC Groups 8-10. Example IUPAC Group 6 metals include molybdenum and tungsten. Example IUPAC Group 8-10 metals include nickel and cobalt.

For example, the catalyst of the hydrotreater 140 may comprise Ni and Mo on an alumina support (sometimes referred to as "Ni—Mo/$Al_2O_3$ catalyst"). The catalyst of the hydrotreater 140 may also contain a dopant that is selected from the group consisting of boron, phosphorus, halogens, silicon, and combinations thereof. In one or more embodiments, the catalyst of the hydrotreater 140 may comprise from 1 wt. % to 25 wt. % of an oxide or sulfide of molybdenum (such as from 11 wt. % to 17 wt. % or from 12 wt. % to 16 wt. % of an oxide or sulfide of molybdenum), from 1 wt. % to 7 wt. % of an oxide or sulfide of nickel (such as from 2 wt. % to 6 wt. % or from 3 wt. % to 5 wt. % of an oxide or sulfide of nickel), and from 75 wt. % to 89 wt. % of alumina (such as from 77 wt. % to 87 wt. % or from 79 wt. % to 85 wt. % of alumina). In some embodiments, the catalyst of the hydrotreater 140 may further comprise cobalt. In one embodiment, the catalyst of the hydrotreater 140 may comprise nickel and molybdenum, and has a nickel to molybdenum mole ratio (Ni/(Ni+Mo)) of 0.1 to 0.3 (such as from 0.1 to 0.2 or from 0.2 to 0.3). In an embodiment that includes cobalt, the mole ratio of (Co+Ni)/Mo may be in the range of 0.25 to 0.85 (such as from 0.25 to 0.5 or from 0.5 to 0.85).

In some embodiments, the hydrotreater 140 may further comprise a demetalization catalyst, which may be upstream of the other catalysts of the hydrotreater 140. In one or more embodiments, the demetalization catalyst may reduce the content of metals such as, without limitation Ni and/or V in the greater boiling point fraction stream 106. The hydrodemetallization catalysts may comprise a support with wide pore diameter (0.4-1.5 cc/g) and sufficient pore volume to capture the metals. The metals may be in the form of organometallic porphins and converted to metals on the catalysts. In some embodiments, the demetalization catalyst may comprise or consist of alumina or silica support with Ni and/or Mo as active phase metals.

According to one or more embodiments, the hydrotreater 140 may have a weighted average bed temperature of from 300° C. to 500° C., such as from 350° C. to 450° C. The hydrotreater 140 may have a LHSV of 0.1/hour to 2/hour, such as from 0.5/hour to 1/hour. The hydrotreater 140 may have a hydrogen to oil ratio of from 100 StLt/liter of oil to 5000 StLt/liter of oil, such as from 500 StLt/liter of oil to 1500 StLt/liter of oil.

In the embodiments described herein, the hydrotreater 120 is operated at a lower pressure than the hydrotreater 140. For example, the hydrotreater 140 may operate at a temperature of at least 25 bar greater than the hydrotreater 140, at least 30 bar greater than the hydrotreater 140, at least 35 bar greater than the hydrotreater 140, at least 40 bar greater than the hydrotreater 140, at least 45 bar greater than the hydrotreater 140, at least 50 bar greater than the hydrotreater 140, at least 60 bar greater than the hydrotreater 140, at least 70 bar greater than the hydrotreater 140, at least 80 bar greater than the hydrotreater 140, at least 90 bar greater than the hydrotreater 140, or even at least 100 bar greater than the hydrotreater 140.

In one or more embodiments, the hydrotreater 120 may operate at a pressure of from 30 bar to 70 bar. For example, the hydrotreater 120 may operate at a pressure of from 30 bar to 35 bar, from 35 bar to 40 bar, from 40 bar to 45 bar, from 45 bar to 50 bar, from 50 bar to 55 bar, from 55 bar to 60 bar, from 60 bar to 65 bar, from 65 bar to 70 bar, or any combination of these ranges.

In one or more embodiments, the hydrotreater 140 may operate at a pressure of at least 120 bar, such as from 120 bar to 200 bar. For example, the hydrotreater 140 may operate at a pressure of from 120 bar to 130 bar, from 130 bar to 140 bar, from 140 bar to 150 bar, from 150 bar to 160 bar, from 160 bar to 170 bar, from 170 bar to 180 bar, from 180 bar to 190 bar, from 190 bar to 200 bar, or any combination of these ranges.

Without being bound by theory, it is believed that separating the hydrocarbon feed stream 102 into the greater boiling point fraction stream 108 and the lesser boiling point fraction stream 108 derives economic efficiencies as described herein. Specifically, the required capital cost of a reactor, such as that utilized as the hydrotreater 120 or the hydrotreater 140, is affected by the operating conditions utilized in the reactor. For example, the reactor capital cost is correlated with the pressure utilized in the reactor. Greater reactor weight is needed for higher pressure reactor conditions, while lesser reactor weights are acceptable for lower pressure reactor conditions, and greater weight reactors have higher capital costs than lesser weight reactors. In the embodiments described herein, it is appreciated that total capital cost is reduced by utilizing two reactors at different pressure operating conditions. This result is recognized largely because the operating pressure in a hydrotreating unit is a function of the heaviest components of the reactant feed. By separately hydrotreating the greater boiling point fraction stream 108 and lesser boiling point fraction stream 108, a lesser pressure can be utilized in the hydrotreater 120, while the hydrotreater 140 can be downsized compared with a case where the entire hydrocarbon feed stream 102 is processed in the same hydrotreating unit. This allows for a greatly reduced combined capital cost of the hydrotreater 120 and the hydrotreater 140 relative to a reactor sized for processing all of the hydrocarbon feed stream 102 at high pressure conditions used in hydrotreater 140.

For example, it has been calculated that when a particular flowrate of the hydrocarbon feed stream 102 is utilized and 50 bar is utilized in the hydrotreater 120, a 138 metric ton (MT) reactor is needed, and when 150 bar is utilized in the hydrotreater 140, a 335 MT reactor is needed (totaling 473 MT of reactor). However, if the entire hydrocarbon feed stream 102 were hydroprocessed in a single reactor at 150 MT (since the same bottoms are present in the hydrocarbon feed stream 102 and the greater boiling point fraction stream 108), 642 MT of reactor are needed. Thus, in this example, a 36% reactor difference is present, greatly reducing capital costs.

Referring still to FIGS. 1 and 2, at least portions of or all of the first hydroprocessed effluent 124 and/or the second hydroprocessed effluent 144 may be cracked. In one or more embodiments, at least a portion of or all of the first hydroprocessed effluent 124 and/or at least a portion of or all of the second hydroprocessed effluent 144 are cracked by fluid catalytic cracking ("FCC"). As is depicted, a first FCC unit 150 and a second FCC unit 160 may be utilized for the cracking. In each of FCC unit 150 and FCC unit 160, the hydrocracked effluents are cracked and a cracking reaction product is formed. A first cracking reaction product 156 may be formed as the effluent of the first FCC unit 150, and a second cracking reaction product 166 may be formed as the effluent of the second FCC unit 160. Such gases may include any leftover hydrogen from the hydroprocessing as well as gasses formed during hydroprocessing or gasses originally contained in hydrocarbon feed stream 102. In such embodiments, "at least a portion" of the first hydroprocessed effluent 124 and/or second hydroprocessed effluent 144 are passed to first and second FCC units 150, 160, respectively. However, it should be understood that "at least a portion of" a stream includes all of the stream.

According to one or more embodiments described herein, the gasses of the first hydroprocessed effluent 124 and/or the gasses of the second hydroprocessed effluent 144 may be separated from liquids prior to cracking. For example, components of the first hydroprocessed effluent 124 that are gasses at atmospheric conditions may be separated as gas stream 125. Similarly, components of the second hydroprocessed effluent 144 that are gasses at atmospheric conditions may be separated as gas stream 145, as is shown in FIGS. 1 and 2.

Now referring only to FIG. 2, in some embodiments gasses present in the first hydroprocessed effluent 124 and/or the second hydroprocessed effluent 144 may be separated from the liquid components in the separation unit 130. It should be noted that the gas stream is not depicted in FIG. 2, but would be separate from streams 132, 134, 136. In such embodiments, no gas streams 125, 145 may be needed since the gasses are removed following injection of the first hydroprocessed effluent 124 and second hydroprocessed effluent 144 into the separation unit 130.

In one or more embodiments, the first FCC unit 150 and the second FCC unit 160 may be fed regenerated or fresh catalyst 154, 164 and may eject spent catalyst 152, 162. The spent catalyst may be regenerated and fed back into the first FCC unit 150 or the second FCC unit 160 as regenerated catalyst 154 or 164, respectively. As would be understood in the art, the catalyst may be regenerated and generally recycled in the system, but new catalyst is needed due to process losses over time.

In general, the first FCC unit 150 and the second FCC unit 160 may operate with different processing conditions and/or catalyst compositions such that the first FCC unit 150 is more efficient in cracking relatively lighter hydrocarbon compositions than the second FCC unit 160, and vice versa.

In one or more embodiments, the first FCC unit 150 may be operated at a temperature of 450° C. to 700° C., such as from 550° C. to 650° C. The first FCC unit 150 may operate at a pressure of from 1 bar to 3 bar, such as from 1 bar to 2 bar or from 2 bar to 3 bar. The first FCC unit 150 may operate with a residence time of from 0.1 seconds to 30 seconds, such as from 0.1 second to 10 seconds, from 10 seconds to 20 seconds, from 20 seconds to 30 seconds, or any combination of these ranges. The catalyst to oil ratio (by weight) in the first FCC unit 150 may be from 6:1 to 60:1, such as from 6:1 to 40:1.

In one or more embodiments, the second FCC unit 160 may be operated at a temperature of 450° C. to 700° C., such as from 550° C. to 650° C. The second FCC unit 160 may operate at a pressure of from 1 bar to 3 bar, such as from 1 bar to 2 bar or from 2 bar to 3 bar. The second FCC unit 160 may operate with a residence time of from 0.1 seconds to 30 seconds, such as from 0.2 second to 10 seconds. The catalyst to oil ratio (by weight) in the second FCC unit 160 may be from 3:1 to 30:1, such as from 3:1 to 20:1.

In one or more embodiments, the catalyst (sometimes referred to as the "base catalyst") utilized in the first FCC unit 150 and/or the second FCC unit 160 may comprise one or more zeolite compositions. A catalyst additive may also be present in some embodiments in the first FCC unit 150, the second FCC unit 160, or both, which may comprise a shape-selective zeolite such as an MFI zeolite. The base catalyst may comprise from 60 wt. % to 95 wt. % of total catalyst in the first FCC unit 150 and/or the second FCC unit 160, and the catalyst additive may comprise from 5 wt. % to 40 wt. % of the total catalyst in the first FCC unit 150 and/or the second FCC unit 160. The base catalyst may comprise zeolite, such as USY zeolite or post modified USY in which some of the framework alumina is replaced by Ti and/or Zr. The base catalyst matrix may comprise alumina and/or clay and/or kaolin materials. The catalyst of the first FCC unit may not include active phase metals, and may rely on the zeolite as the primary source of catalytic functionality.

In one or more embodiments, the base catalyst in the first FCC unit 150 and/or the second FCC unit 160 may have a bulk density of 0.5 g/ml to 1.0 g/ml, an average particle diameter of 50 microns to 90 microns, a surface area of 50 $m^2/g$ to 350 and a pore volume of 0.05 ml/g to 0.5 ml/g.

In one or more embodiments, the zeolite of the catalyst additive may comprise a zeolite that is characterized by an average pore diameter that is less than the average pore diameter of Y-type zeolite. The zeolite of the catalyst additive may be selected from the group consisting of ZSM-5 zeolite, beta zeolite, zeolite omega, SAPO-5 zeolite, SAPO-11 zeolite, SAPO-34 zeolite, pentasil-type aluminosilicate, and combinations comprising at least one of the foregoing shape selective zeolite. The zeolite of the catalyst additive may have a bulk density of 0.5 g/ml to 1.0 g/ml, an average particle diameter of 50 microns to 90 microns, a surface area of 10 $m^2/g$ to 200 $m_2/g$ and a pore volume of 0.01 ml/g to 0.70. In one or more embodiments, the catalyst additive comprises from 20 wt. % to 70 wt. %, such as from 30 wt. % to 60 wt. %, of zeolite.

System 100 of FIG. 1 and system 101 of FIG. 2 are similar in many respects, but vary in what streams are passed into the first FCC unit 150 and the second FCC unit 160. Referring to FIG. 1, at least a portion of the first hydroprocessed effluent 124 is passed directly to the first FCC unit 150 and at least a portion of the second hydroprocessed effluent 144 is passed directly to the second FCC unit 160. However, this is not the case in system 101 of FIG. 2. In system 101, at least a portion of the first hydroprocessed effluent 124 and at least a portion of the second hydroprocessed effluent 144 are passed to a separation unit 130. At least a portion of the first hydroprocessed effluent 124 and at least a portion of the second hydroprocessed effluent 144 may be combined prior to entering the separation unit 130 as shown in FIG. 2, or they may be each separately passed to the separation unit 130.

The separation unit 130 may separate the components of at least a portion of the first hydroprocessed effluent 124 and at least a portion of the second hydroprocessed effluent 144 (for example, the liquid components of these streams) into three streams 132, 134, 136. Stream 136 may be heavier than stream 134, and stream 134 may be heavier than stream 132. As such, stream 132 may be described as a light stream, stream 134 may be described as a medium stream, and stream 136 may be described as a heavy stream. In one or more embodiments, stream 134 comprises, consists essentially off, or consists of hydrotreated diesel. Stream 132 may be passed to the first FCC unit 150 and stream 136 may be passed to the second FCC unit 160. In additional embodiments, stream 134 may be utilized as a product stream and comprise at least a portion or all of diesel product. Alternatively, stream 134 may be sent to the first FCC unit 150 or the second FCC unit 160.

Referring again to FIGS. 1 and 2, the first cracking reaction product stream 156 and the second cracking reaction product stream 166 each may include a mixture of cracked hydrocarbon materials, which may be further separated into one or more greater value petrochemical products and recovered from the system in the one or more system product streams. For example, the first cracking reaction product stream 156, the second cracking reaction product stream 166, or both, may include one or more of propylene, gasoline, light cycle oil, heavy cycle oil, unrecoverable bottoms, or combinations of these.

The hydrocarbon feed conversion systems 100 and 101 may include a product separator 170, such as any suitable separation unit. The first cracking reaction product stream 156, the second cracking reaction product stream 166, or both the first and second cracking reaction product streams 156, 166, may be introduced to the product separator 170 to separate these streams into a plurality of system product streams 172, 174, 176, 178 including dry gas (C1+C2) (not depicted in the figures), propylene 172, LPG (C3-C4 paraffins) (not depicted in the figures), butylenes (C4 olefins) (not depicted in the figures), gasoline 174, light cycle oil 176, heavy cycle oil 178, and unrecoverable bottoms 180. It should be appreciated that the product separator 170 may be customized to deliver whatever product stream is desired assuming that such product materials are present in the feed stream passed to the product separator 170. The product separator 170 may be a distillation column or collection of separation devices that separates the first cracking reaction product stream 156, the second cracking reaction product stream 166, or a stream including both.

In one or more embodiments, a portion or all of the light cycle oil 176 and/or the heavy cycle oil 178 may be recycled in the system. For example, either recycle stream 182 and/or 184 may be combined with the greater boiling point fraction stream 106, the lesser boiling point fraction stream 108, or both.

EXAMPLES

The various embodiments of methods and systems for the conversion of crude oils will be further clarified by the following example. The example is illustrative in nature, and should not be understood to limit the subject matter of the present disclosure.

Example 1

The system depicted in FIG. 2 was utilized as the basis for this example. However, it should be understood that the data shown is derived from experimental reaction data utilizing the specified oil cuts and catalysts. That is, no computer simulation was utilized but, rather, calculations were made to determine the mass flow rate and composition of particular streams in a system such as that in FIG. 2. In the example, 1000 kg/h of heavy crude oil was processed to produce value added products. Properties and composition of the crude oil are shown in Table 2. The operating conditions for each unit are summarized in Table 3, and the material balance for the key streams are provided in Table 4. The FCC units utilized a catalyst and additive.

The catalyst contained post modified USY zeolite as well as other catalyst components such as kaolin and other clay minerals, activated alumina, porous silica, and rare-earth metal compounds. The catalyst additive contained ZSM-5 zeolite.

It is noted that Table 4 does not include a full material balance, as it does not include light gases, $C_1$-$C_4$, $H_2S$, $NH_3$, and FCC coke.

TABLE 2

| Property | Unit | Value |
| --- | --- | --- |
| Density | Kg/Lt | 0.904 |
| API Gravity | ° | 25.0 |
| Sulfur | W % | 3.00 |
| Nitrogen | ppmw | 1728 |
| MCR | W % | 8.2 |

TABLE 2-continued

| Property | Unit | Value |
| --- | --- | --- |
| Nickel | ppmw | 19 |
| Vanadium | ppmw | 59 |
| Naphtha (36-204° C.) | Kg/h | 176 |
| Mid-Distillate (204-370° C.) | Kg/h | 266 |
| Atmospheric residue (370° C.+) | Kg/h | 559 |

TABLE 3

| Variable\Vessel | Units | 120 | 140 | 150 | 160 |
| --- | --- | --- | --- | --- | --- |
| Temperature | ° C. | 320 | 370 | 650 | 650 |
| Hydrogen Pressure | Bar | 45 | 140 | 1 | 1 |
| LHSV | $h^{-1}$ | 1 | 0.5 | 2 | 2 |
| Cat/Oil Ratio | — | — | — | 30 | 30 |
| Catalyst | | Ni-Co-Mo/Al | Ni-Mo/Al | FCC Cat + Add. | FCC Cat + Add. |

TABLE 4

| Stream # | Units | 102 | 106 | 108 | 132 | 134 | 136 | 172 | 174 | 176 | 178 |
| --- | --- | --- | --- | --- | --- | --- | --- | --- | --- | --- | --- |
| Feedrate | Kg/h | 1000 | 559 | 442 | 184 | 327 | 482 | 135 | 262 | 31 | 20 |
| Density | Kg/Lt | 0.904 | 0.989 | 0.798 | 0.738 | 0.851 | 0.978 | | 0.746 | 0.970 | 1.080 |
| API Gravity | ° | 25.0 | 11.6 | 45.9 | 60.2 | 34.8 | | | 58.3 | 14.4 | −0.5 |
| Sulfur | W % | 3.00 | 4.64 | 0.92 | 10 | 10 | 0.31 | | | | |
| Nitrogen | ppmw | 1728 | 3059 | 44 | 1 | 10 | 1468 | | | | |
| MCR | W% | 8.2 | 14.7 | 0.0 | 0 | 0 | 4.41 | | | | |
| Nickel | ppmw | 19 | 34 | 0 | 0 | 0 | 3.45 | | | | |
| Vanadium | ppmw | 59 | 106 | 0 | 0 | 0 | 10.60 | | | | |
| Composition | wt.% | | | | | | | | | | |
| Propylene | Kg/h | | | | | | | 135 | | | |
| Naphtha (36-204° C.) | Kg/h | 176 | — | 176 | 184 | — | 0 | 0 | 262 | 0 | 0 |
| Mid-Distillate (204-370° C.) | Kg/h | 266 | — | 266 | | 327 | 0 | 0 | 0 | 31 | 0 |
| Atmospheric residue (370° C.+) | Kg/h | 559 | 559 | | | | 482 | | | | 20 |

According to a first aspect of the present application, petrochemical products may be formed from a hydrocarbon material by a process that may comprise separating the crude oil into at least a lesser boiling point fraction and a greater boiling point fraction. At least 90 wt. % of the crude oil may be present in the combination of the greater boiling point fraction and the lesser boiling point fraction. The process may further comprise hydroprocessing the lesser boiling point fraction to form a first hydroprocessed effluent and hydroprocessing the greater boiling point fraction to form a second hydroprocessed effluent. The hydroprocessing of the lesser boiling point fraction may occur at a first pressure, the hydroprocessing of the lesser boiling point fraction may occur at a second pressure, and the second pressure may be at least 25 bar greater than the first pressure. The method may further comprise cracking at least a portion of the first hydroprocessed effluent and at least a portion of the second hydroprocessed effluent to form cracking reaction products.

A second aspect includes any of the aspects described herein, wherein at least 99 wt. % of the crude oil is present in the combination of the greater boiling point fraction and the lesser boiling point fraction.

A third aspect includes any of the aspects described herein, wherein the first pressure is from 30 bar to 70 bar.

A fourth aspect includes any of the aspects described herein, wherein the second pressure is from 120 bar to 200 bar.

A fifth aspect includes any of the aspects described herein, wherein the first hydroprocessed effluent and the second hydroprocessed effluent are cracked by fluid catalytic cracking.

A sixth aspect includes any of the aspects described herein, wherein the hydroprocessing of the lesser boiling point fraction reduces the sulfur content and the nitrogen content in the lesser boiling point fraction.

A seventh aspect includes any of the aspects described herein, wherein the hydroprocessing of the greater boiling point fraction reduces the sulfur content, the nitrogen content, the metals content, asphaltenes, and aromatics content in the lesser boiling point fraction.

An eighth aspect includes any of the aspects described herein, wherein the difference between the 5 wt. % boiling point and the 95 wt. % boiling point of the crude oil is at least 100° C.

A ninth aspect includes any of the aspects described herein, wherein the cut point of the lesser boiling point fraction and the greater boiling point fraction is from 350° C. to 400° C.

A tenth aspect includes any of the aspects described herein, wherein the cracking reaction products comprise propylene.

According to an eleventh aspect of the present application, petrochemical products may be formed from a hydrocarbon material by a process that may comprise separating the crude oil into at least a lesser boiling point fraction and a greater boiling point fraction. At least 90 wt. % of the crude oil may be present in the combination of the greater boiling point fraction and the lesser boiling point fraction. The process may further comprise hydroprocessing the lesser boiling point fraction to form a first hydroprocessed effluent and hydroprocessing the greater boiling point fraction to form a second hydroprocessed effluent. The hydroprocessing of the lesser boiling point fraction may occur at a first pressure, the hydroprocessing of the lesser boiling point fraction may occur at a second pressure, and the second pressure may be at least 25 bar greater than the first pressure. The process may further comprise passing at least a portion of the first hydroprocessed effluent to a first FCC unit and cracking at least a portion of the first hydroprocessed effluent in the first FCC unit and passing at least a portion of the second hydroprocessed effluent to a first FCC unit and cracking at least a portion of the second hydroprocessed effluent in the second FCC unit.

A twelfth aspect includes any of the aspects described herein, wherein at least 99 wt. % of the crude oil is present in the combination of the greater boiling point fraction and the lesser boiling point fraction.

A thirteenth aspect includes any of the aspects described herein, wherein the first pressure is from 30 bar to 70 bar.

A fourteenth aspect includes any of the aspects described herein, wherein the cut point of the lesser boiling point fraction and the greater boiling point fraction is from 350° C. to 400° C.

A fifteenth aspect includes any of the aspects described herein, wherein the second pressure is from 120 bar to 200 bar.

According to a sixteenth aspect of the present application, petrochemical products may be formed from a hydrocarbon material by a process that may comprise separating the crude oil into at least a lesser boiling point fraction and a greater boiling point fraction. At least 90 wt. % of the crude oil may be present in the combination of the greater boiling point fraction and the lesser boiling point fraction. The process may further comprise hydroprocessing the lesser boiling point fraction to form a first hydroprocessed effluent and hydroprocessing the greater boiling point fraction to form a second hydroprocessed effluent. The hydroprocessing of the lesser boiling point fraction may occur at a first pressure, the hydroprocessing of the lesser boiling point fraction may occur at a second pressure, and the second pressure may be at least 25 bar greater than the first pressure. The process may further comprise passing at least a portion of the first hydroprocessed effluent and at least a portion of the second hydroprocessed effluent to a separation unit to form a light fraction, a middle fraction, and a heavy fraction. The process may further comprise passing the light fraction to a first FCC unit and cracking the second hydroprocessed effluent in the first FCC unit and passing the heavy fraction to a second FCC unit and cracking the second hydroprocessed effluent in the second FCC unit.

A seventeenth aspect includes any of the aspects described herein, wherein at least 99 wt. % of the crude oil is present in the combination of the greater boiling point fraction and the lesser boiling point fraction.

An eighteenth aspect includes any of the aspects described herein, wherein the first pressure is from 30 bar to 70 bar and the second pressure is from 120 bar to 200 bar.

A nineteenth aspect includes any of the aspects described herein, wherein the cut point of the lesser boiling point fraction and the greater boiling point fraction is from 350° C. to 400° C.

A twentieth aspect includes any of the aspects described herein, further comprising collecting the middle fraction as a diesel product.

For the purposes of defining the present technology, the transitional phrase "consisting of" may be introduced in the claims as a closed preamble term limiting the scope of the claims to the recited components or steps and any naturally occurring impurities.

For the purposes of defining the present technology, the transitional phrase "consisting essentially of" may be introduced in the claims to limit the scope of one or more claims to the recited elements, components, materials, or method steps as well as any non-recited elements, components, materials, or method steps that do not materially affect the novel characteristics of the claimed subject matter.

The transitional phrases "consisting of" and "consisting essentially of" may be interpreted to be subsets of the open-ended transitional phrases, such as "comprising" and "including," such that any use of an open ended phrase to introduce a recitation of a series of elements, components, materials, or steps should be interpreted to also disclose recitation of the series of elements, components, materials, or steps using the closed terms "consisting of" and "consisting essentially of." For example, the recitation of a composition "comprising" components A, B and C should be interpreted as also disclosing a composition "consisting of" components A, B, and C as well as a composition "consisting essentially of" components A, B, and C.

Any quantitative value expressed in the present application may be considered to include open-ended embodiments consistent with the transitional phrases "comprising" or "including" as well as closed or partially closed embodiments consistent with the transitional phrases "consisting of" and "consisting essentially of."

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a stream or in a reactor should be appreciated as containing, in some embodiments, a mixture of isomers of that constituent. For example, a compositional range specifying butylene may include a mixture of various isomers of butylene. It should be appreciated that the examples supply compositional ranges for various streams, and that the total amount of isomers of a particular chemical composition can constitute a range.

The subject matter of the present disclosure has been described in detail and by reference to specific embodiments. It should be understood that any detailed description of a component or feature of an embodiment does not necessarily imply that the component or feature is essential to the particular embodiment or to any other embodiment. Further, it should be apparent to those skilled in the art that various modifications and variations can be made to the described embodiments without departing from the spirit and scope of the claimed subject matter.

What is claimed is:

1. A process for producing petrochemical products from crude oil, the process comprising:
    separating the crude oil into at least a lesser boiling point fraction and a greater boiling point fraction, wherein at least 90 wt. % of the crude oil is present in the combination of the greater boiling point fraction and the lesser boiling point fraction;
    hydroprocessing the lesser boiling point fraction to form a first hydroprocessed effluent, wherein the hydroprocessing of the lesser boiling point fraction occurs at a first pressure;
    hydroprocessing the greater boiling point fraction to form a second hydroprocessed effluent, wherein the hydroprocessing of the greater boiling point fraction occurs at a second pressure, and wherein the second pressure is at least 25 bar greater than the first pressure; and
    cracking at least a portion of the first hydroprocessed effluent and at least a portion of the second hydroprocessed effluent to form cracking reaction products.

2. The process of claim 1, wherein at least 99 wt. % of the crude oil is present in the combination of the greater boiling point fraction and the lesser boiling point fraction.

3. The process of claim 1, wherein the first pressure is from 30 bar to 70 bar.

4. The process of claim 1, wherein the second pressure is from 120 bar to 200 bar.

5. The process of claim 1, wherein at least a portion of the first hydroprocessed effluent and at least a portion of the second hydroprocessed effluent are cracked by fluid catalytic cracking.

6. The process of claim 1, wherein the hydroprocessing of the lesser boiling point fraction reduces the sulfur content and the nitrogen content in the lesser boiling point fraction.

7. The process of claim 1, wherein the hydroprocessing of the greater boiling point fraction reduces the sulfur content, the nitrogen content, the metals content, asphaltenes, and aromatics content in the greater boiling point fraction.

8. The process of claim 1, wherein the difference between the 5 wt. % boiling point and the 95 wt. % boiling point of the crude oil is at least 100° C.

9. The process of claim 1, wherein the cut point of the lesser boiling point fraction and the greater boiling point fraction is from 350° C. to 400° C.

10. The process of claim 1, wherein the cracking reaction products comprise propylene.

11. A process for producing petrochemical products from crude oil, the process comprising:
    separating the crude oil into at least a lesser boiling point fraction and a greater boiling point fraction, wherein at least 90 wt. % of the crude oil is present in the combination of the greater boiling point fraction and the lesser boiling point fraction;
    hydroprocessing the lesser boiling point fraction to form a first hydroprocessed effluent, wherein the hydroprocessing of the lesser boiling point fraction occurs at a first pressure;
    hydroprocessing the greater boiling point fraction to form a second hydroprocessed effluent, wherein the hydroprocessing of the greater boiling point fraction occurs at a second pressure, and wherein the second pressure is at least 25 bar greater than the first pressure; and
    passing the at least a portion of the first hydroprocessed effluent to a first FCC unit and cracking at least a portion of the first hydroprocessed effluent in the first FCC unit;
    passing at least a portion of the second hydroprocessed effluent to a second FCC unit and cracking at least a portion of the second hydroprocessed effluent in the second FCC unit.

12. The process of claim 11, wherein at least 99 wt. % of the crude oil is present in the combination of the greater boiling point fraction and the lesser boiling point fraction.

13. The process of claim 11, wherein the first pressure is from 30 bar to 70 bar.

14. The process of claim 11, wherein the cut point of the lesser boiling point fraction and the greater boiling point fraction is from 350° C. to 400° C.

15. The process of claim 11, wherein the second pressure is from 120 bar to 200 bar.

16. A process for producing petrochemical products from crude oil, the process comprising:
    separating the crude oil into at least a lesser boiling point fraction and a greater boiling point fraction, wherein at least 90 wt. % of the crude oil is present in the combination of the greater boiling point fraction and the lesser boiling point fraction;
    hydroprocessing the lesser boiling point fraction to form a first hydroprocessed effluent, wherein the hydroprocessing of the lesser boiling point fraction occurs at a first pressure;
    hydroprocessing the greater boiling point fraction to form a second hydroprocessed effluent, wherein the hydroprocessing of the greater boiling point fraction occurs at a second pressure, and wherein the second pressure is at least 25 bar greater than the first pressure; and
    passing at least a portion of the first hydroprocessed effluent and at least a portion of the second hydroprocessed effluent to a separation unit to form a light fraction, a middle fraction, and a heavy fraction;
    passing the light fraction to a first FCC unit and cracking the second hydroprocessed effluent in the first FCC unit; and
    passing the heavy fraction to a second FCC unit and cracking the second hydroprocessed effluent in the second FCC unit.

17. The process of claim 16, wherein at least 99 wt. % of the crude oil is present in the combination of the greater boiling point fraction and the lesser boiling point fraction.

18. The process of claim 16, wherein the first pressure is from 30 bar to 70 bar and the second pressure is from 120 bar to 200 bar.

19. The process of claim 16, wherein the cut point of the lesser boiling point fraction and the greater boiling point fraction is from 350° C. to 400° C.

20. The process of claim 16, further comprising collecting the middle fraction as a diesel product.

\* \* \* \* \*